United States Patent [19]
Miura et al.

[11] Patent Number: 4,811,593
[45] Date of Patent: Mar. 14, 1989

[54] VISCOSITY DETECTOR

[75] Inventors: Shinsuke Miura; Susumu Ishizuka, both of Tokyo, Japan

[73] Assignee: Yamaichi Electric Mfg. Co., Ltd., Tokyo, Japan

[21] Appl. No.: 125,602

[22] Filed: Nov. 25, 1987

[30] Foreign Application Priority Data

Nov. 27, 1986 [JP] Japan .................. 61-282586

[51] Int. Cl.⁴ .................................. G01N 11/10
[52] U.S. Cl. ............................................ 73/54
[58] Field of Search ......................... 73/54, 32 A

[56] References Cited

U.S. PATENT DOCUMENTS 4,193,291 3/1980 Lynnworth .................. 73/32 A
4,240,285 12/1980 Langdon ..................... 73/32 A Primary Examiner—Stewart J. Levy
Assistant Examiner—Joseph W. Roskos
Attorney, Agent, or Firm—Wenderoth, Lind & Ponack

[57] ABSTRACT

A viscosity detector includes an electromechanical vibrator having a central axis and capable of vibrating about the central axis, a transmission shaft having one end thereof connected coaxially to the vibrator, and a detector member connected coaxially to the other end of the transmission shaft. The detector member is immersed in liquid the viscosity of which is to be measured, and is vibrated about the central axis of the vibrator within the liquid by the vibration of the vibrator transmitted through the transmission shaft to detect the viscous resistance of the liquid at a circumferential surface of the detector member. The vibrator converts the detected viscous resistance into an electric signal.

2 Claims, 4 Drawing Sheets

VISCOSITY DETECTOR

BACKGROUND OF THE INVENTION AND RELATED ART STATEMENT

The present invention relates to a viscosity detector using an electromechanical vibrator which comprises piezoelectric ceramic members, for example, and vibrates about its central axis, and has a detector member which is immersed in liquid to measure the viscosity thereof and which is vibrated about its central axis, which central axis is coaxial with the central axis of the electromechanical vibrator, via the electromechanical vibrator to measure the viscosity of the liquid based on viscous resistance offered by the liquid.

The present inventors conducted studies on a viscosity detector and conceived a method of measuring the viscosity of liquid by using an electromechanical vibrator, connecting the vibrator to a detector member, immersing the detector member within the liquid, transmitting the vibration of the vibrator to the detector member, detecting viscous resistance offered by the liquid and converting the viscous resistance into an equivalent electric signal. In accordance with their idea, they tried to use a commercially available vibrator vibrating in the direction of its thickness as the electromechanical vibrator. As a result, it was found that the vibrator connected to a detector member caused the detector member to be vibrated vertically relative to the surface of liquid, thereby producing vibration waves propagating within the liquid and thus making it difficult to measure the viscosity of the liquid with a high degree of precision. In view of this, they used a vibrator member having a small wall thickness and tried to vibrate it in a direction parallel to the surface thereof. As a result, however, it was found that it was difficult to vibrate the vibrator member while in a state of being held precisely parallel to the surface thereof due to deviation in the center thereof produced during the operation of the vibration, that the problem of the generation of wave motion was insufficiently solved, that restrictions were present with respect to the surface area of the detector member, to the sensitivity of the detector member to the viscous resistance and to the range of viscosity measurement and therefore that it was difficult to measure the viscosity with a high degree of precision. The inventors have come to a conclusion that the detector member should be stably vibrated within the liquid while the liquid is maintained in a state as static as possible.

OBJECT AND SUMMARY OF THE INVENTION

The main object of the present invention is to provide a viscosity detector of having a simple construction, and that is small, light, capable of effectively preventing the generation of a wave, which is a disturbance factor, within the liquid, highly sensitive to the viscous resistance of the liquid, and is also capable of measuring the viscosity of the liquid over a wide range with a high degree of precision.

To attain the object described above, according to the present invention, there is provided a viscosity detector comprising an electromechanical vibrator having a central axis and capable of vibrating about the central axis, a transmission shaft having one end thereof connected coaxially to the vibrator, and a detector member connected coaxially to the other end of the transmission shaft, the detector member being immersed in liquid, the viscosity of which is to be measured, and vibrated about the central axis of the vibrator within the liquid by the vibration of the vibrator transmitted through the transmission shaft to detect viscous resistance of the liquid at a circumferential surface thereof, the vibrator converting the detected viscous resistance into an electric signal.

The above and other objects, characteristic features and advantages of the present invention will become more apparent to those skilled in the art by the following description of the preferred embodiment of the invention, as illustrated in the accompanying drawings.

DETAILED DESCRIPTION OF THE PREFERRED EMBODIMENT

Figure 1:
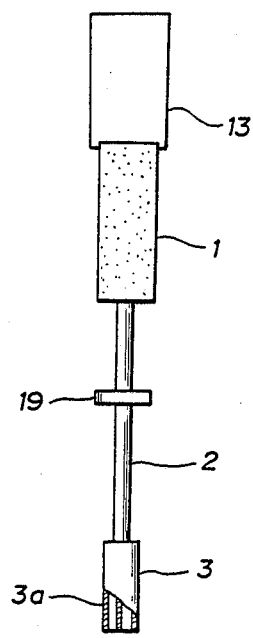
FIG. 1 is a side view illustrating the detection structure of one embodiment of the viscosity detector according to the present invention.
Figure 5:
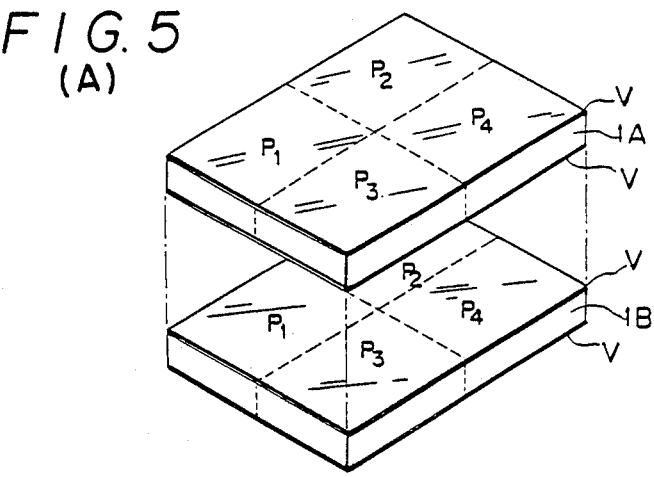
FIG. 5(A) is an exploded perspective view illustrating one example of the vibrator.
FIG. 5(B) is a side view illustrating the vibrator of FIG. 5(A).
Figure 5:
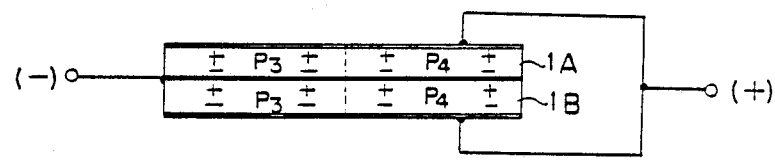
Figure 6:
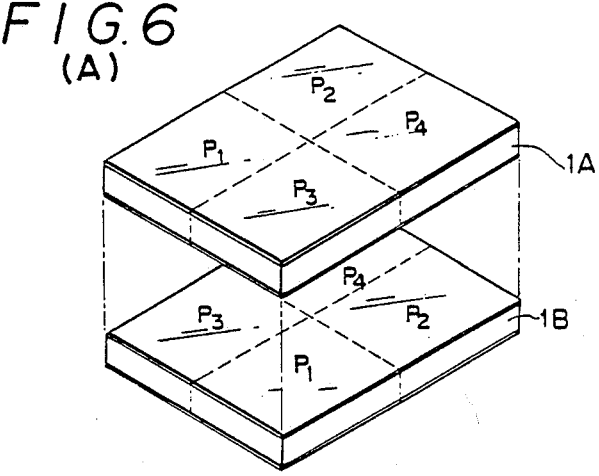
FIG. 6(A) is an exploded perspective view illustrating another example of the vibrator.
FIG. 6(B) is a side view illustrating the vibrator of FIG. 6(A).
Figure 6:
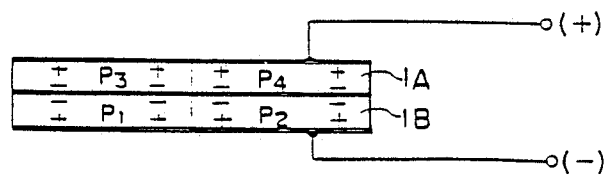
Figure 7:
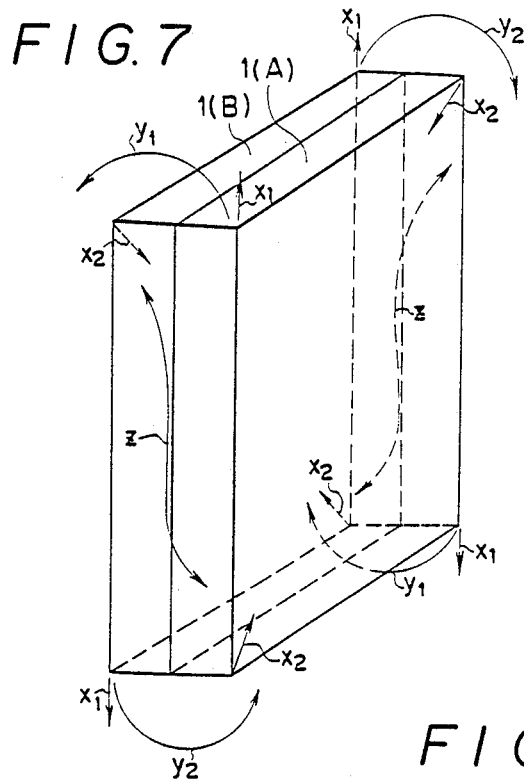
FIG. 7 is an explanatory perspective view illustrating twist vibration of the vibrator of FIG. 5(A) of FIG. 6(A).

The present invention will now be described with reference to the illustrated embodiment. FIG. 1 is a side view illustrating a detection structure of one embodiment of the viscosity detector according to the present invention. The detection structure comprises an electromechanical vibrator 1, which will be described in detail later with reference to FIGS. 5 to 7, a transmission shaft 2 connected at one end thereof coaxially to one end of the vibrator 1, and a detector member 3 connected coaxially to the other end of the transmission shaft 2, whereby the detector member 3 can be vibrated about the common axis by the vibration of the vibrator 1 transmitted through the transmission shaft 2.

The transmission shaft 2 has the shape of a column or square pillar and serves not only as a carrier for supporting the detector member 3 at a location spaced from the vibrator 1 but also serves as a vibration transmission medium. The wavelength of a resonance wave propagating along the transmission shaft 2 when resonating is a function of the length of the transmission shaft 2. A mass 19 having a constant moment of inertia may be coaxially fitted about the transmission shaft 2 so that the resonant frequency of the vibrator 1 can be adjusted.

Figure 10:
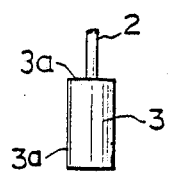
FIGS. 10(A) to 10(D) are side views illustrating examples of detector members.
Figure 10:
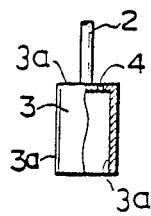
Figure 10:
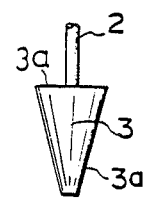
Figure 10:
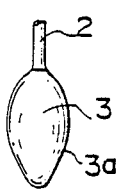

The detector member 3 is a solid column or disk having a circular cross section as illustrated in FIG. 10(A) and is made of metal or synthetic resin, and has a circumferential surface $3a$ having a comparatively large surface area and subjected to mirror surface finishing. The detector member 3 may be a hollow column having a circular cross section, a cone or a spindle as illustrated in FIG. 10(B), 10(C) or 10(D). In the hollow column used as the detector member 3, as illustrated in FIG. 10(B), the bottom wall thereof has at least one air relief hole 4 formed therein.

With the detection structure mentioned above, the vibration of the vibrator 1 about its central axis is transmitted through the transmission shaft 2 to the detector member 3, which vibrates about the common central axis of the vibrator 1, transmission shaft 2 and detector member 3 and detects the viscous resistance of liquid 9 at the circumferential surface $3a$ thereof. The detector member 3 vibrating about the common central axis does not generate a wave which would be a disturbance factor as does a vibrator vibrating in the direction of its thickness direction, thereby maintaining the liquid 9 in a static state and being only subjected to the viscous resistance.

The mechanical viscous resistance detected by the circumferential surface $3a$ of the detector member 3 is converted into an equivalent electric signal by the vibrator 1 to measure the viscosity. Specifically, when the detector member 3 has detected the viscous resistance, the detected viscous resistance is transmitted to the vibrator 1 through the transmission shaft 2 to vary the mechanical impedance obtained at the time of driving the vibrator 1 at a given resonant frequency. The vibrator 1 converts the variation in impedance corresponding to the viscous resistance detected by the circumferential surface $3a$ of the detector member 3 into an equivalent electric signal to measure the viscosity of the liquid 9. This function is effected by the conversion between the electric energy and the mechanical energy of a vibrator formed of piezoelectric ceramic members.

Figure 2:
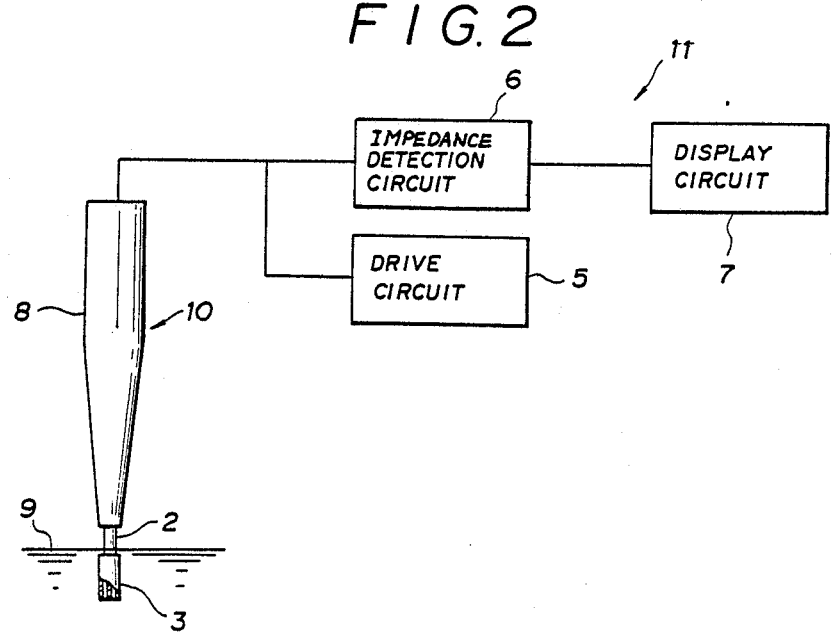
FIG. 2 is a schematic view illustrating the embodiment of FIG. 1 and detection circuit means connected thereto.

As illustrated in FIG. 2, a measuring device 11 detection circuit means which comprises a drive circuit 5 for electrically driving the vibrator 1, an impedance detection circuit 6 for detecting, as an electric signal, the mechanical impedance obtained during the drive of the vibrator at a given resonant frequency, and a display circuit 7 operable in response to the variation in impedance to display the viscosity, and which is connected to the vibrator 1.

Figure 3:
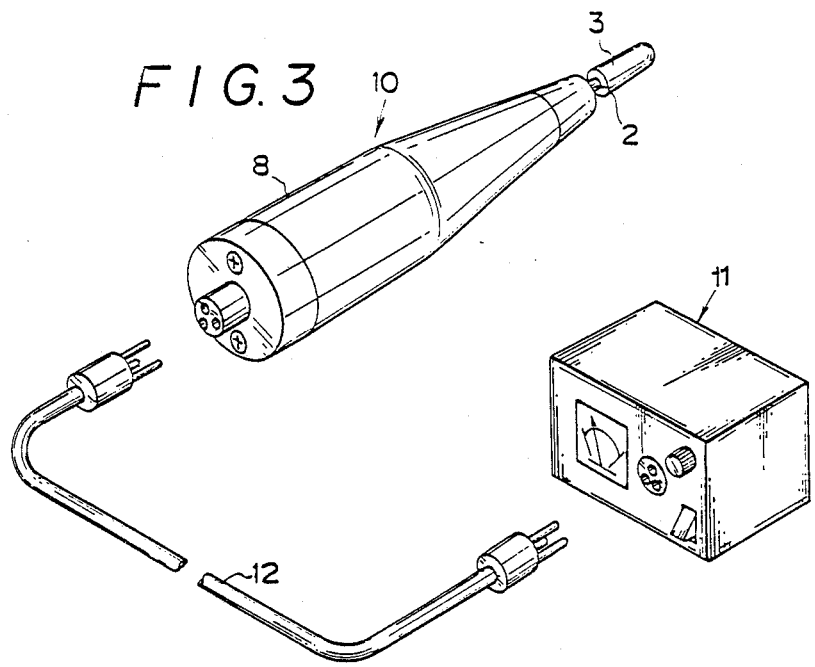
FIG. 3 is a perspective view illustrating a detection section incorporating part of the detection structure, and a measuring device.

As illustrated in FIG. 3, part of the transmission shaft 2 and the entire detector member 3 are exposed, whereas the remaining part of the transmission shaft 2 and the entire vibrator 1 are incorporated into a handgrip type housing 8. The exposed detector member 3 is immersed in the liquid 9 as illustrated in FIG. 2. A detection section 10 is connected via a connector cable 12 to the measuring device 11 comprising the detection circuit means as illustrated in FIG. 3.

The electromechanical vibrator 1 vibrating about its central axis will now be described. FIGS. 5(A) and 5(B) illustrate one example of the vibrator which comprises a pair of piezoelectric ceramic members 1A and 1B having a rectangular shape and attached to each other. Each of the piezoelectric ceramic members 1A and 1B is divided into four quadrants $P_1$, $P_2$, $P_3$ and $P_4$. The two diagonal quadrants $P_1$ and $P_4$ constitute negative-direction polarization sections and the two remaining diagonal quadrants $P_2$ and $P_3$ constitute positive-direction polarization sections. Furthermore, the upper and lower surfaces of each of the piezoelectric ceramic members 1A and 1B are coated with electrodes V. The two piezoelectric ceramic members 1A and 1B are attached to each other so that the lengthwise vibration of the positive-direction polarization sections $P_2$ and $P_3$ is opposite to that of the negative-direction polarization sections $P_1$ and $P_4$ when voltage is applied to the two piezoelectric ceramic members 1A and 1B. To be specific, in a parallel circuit, the two piezoelectric ceramic members 1A and 1B are attached to each other, as illustrated in FIG. 5(B), so that the sections $P_1$, $P_2$, $P_3$ and $P_4$ of one member respectively face the sections $P_1$, $P_2$, $P_3$ and $P_4$ of the other member.

FIGS. 6(A) and 6(B) illustrate another example of the vibrator 1, wherein two piezoelectric ceramic members 1A and 1B each having the upper and lower surfaces thereof coated with electrodes V are attached to each other so that the sections $P_1$, $P_2$, $P_3$ and $P_4$ of one member face the sections $P_3$, $P_4$, $P_1$ and $P_2$ of the other member, respectively. This arrangement of the positive-direction and negative-direction polarization sections can advantageously be used in a series circuit as illustrated in FIG. 6(B).

With the arrangement illustrated in FIG. 5(B) or 6(B), one of a pair of facing sections elongates and the other contracts to allow the pair of facing sections to be bent to one side of the vibrator with respect to the direction of thickness, whereas one of an adjacent pair of facing sections contracts and the other elongates to allow the adjacent pair of facing sections to be bent to the other side of the vibrator with respect to the direction of thickness. Thus, twist vibration is induced. This will be described more specifically below with reference to FIG. 7.

With regard to the positive-direction polarlization sections $P_2$ and $P_3$, the piezoelectric ceramic member 1A elongates in the direction of $x_1$, whereas the piezoelectric ceramic member 1B contracts in the direction of $x_2$. In this case, therefore, the positive-direction polarization sections $P_2$ and $P_3$ are bent to one side with respect to the thickness direction, i.e. in the direction of $y_1$. With regard to the negative-direction polarization sections $P_1$ and $P_4$, the piezoelectric ceramic member 1A contracts in the direction of $x_2$, whereas the piezoelectric member 1B elongates in the direction of $x_1$. In this case, therefore, the negative-direction polarization sections $P_1$ and $P_4$ are bent to the other side with respect to the thickness direction, i.e. in the direction of $y_2$. In this way, the vibrator 1 vibrates in the clockwise direction at one end thereof and in the counterclockwise direction at the other end to produce twist vibration about the central axis thereof.

Figure 4:
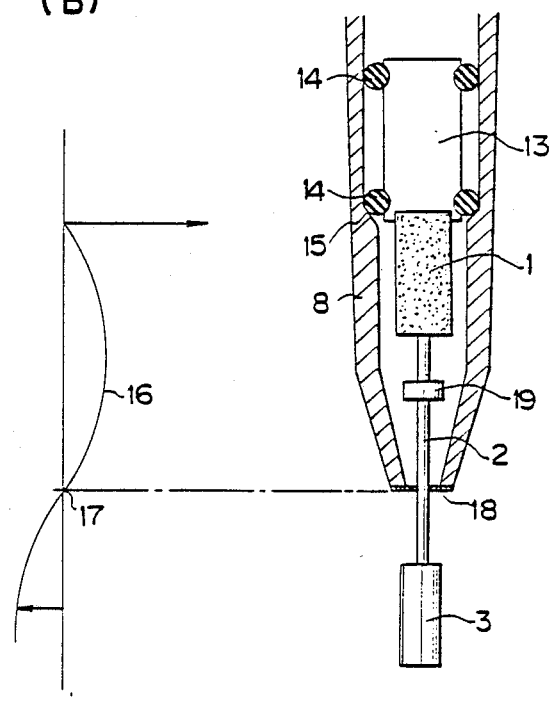
FIG. 4(A) is a longitudinal sectional view illustrating the detection section.
FIG. 4(B) is a diagram illustrating a waveform of a resonance wave of an electromechanical vibrator vibrating about its central axis.

The vibrator 1 having one end thereof connected to the transmission shaft 2 has the other end thereof fixed integrally to an inertia mass 13 as illustrated in FIG. 1 or FIG. 4(A). The inertia mass 13 is incorporated into the housing 8 and is fixed therein by vibration absorbing members 14 tightly fitted on the inner wall of the housing 8 under friction and supported on a receiving portion 15 formed inside the housing 8. Thus, the inertia mass is prevented from moving and is maintained in position as illustrated in FIG. 4(A). The vibrator 1 is vibrated at a resonant frequency so that a node 17 of resonance wave having a waveform 16 is located on the transmission shaft 2, e.g. on the leading end of the housing 8 which is sealed with a sealing member 18, as illustrated in FIG. 4(B). The sealing member 18 supports the transmission shaft 2 and prevents the liquid 9 from entering the housing 8.

Since one end of the vibrator 1 is fixed to the inertia mass 13, as described above, the other end of the vibrator 1 vibrates about its central axis and the vibration thereof is transmitted to the detector member 3 through the transmission shaft 2, thereby vibrating the detector member 3 about the transmission shaft 2 to detect the viscous resistance of the liquid 9 at the circumferential surface 3a of the detector member 3.

Figure 8:
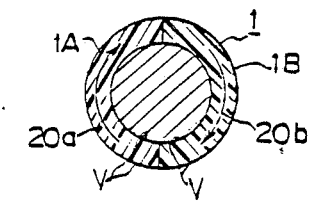
FIG. 8 is a cross-sectional view illustrating still another example of the vibrator.
Figure 9:
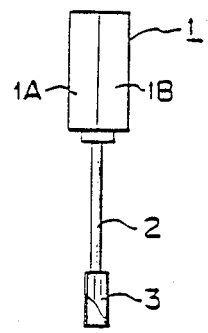
FIG. 9 is a side view illustrating the detection structure having the vibrator of FIG. 8.

FIGS. 8 and 9 illustrate still another example of the vibrator 1. In this example, the vibrator 1 is formed of piezoelectric ceramic material having in the shape of a hollow cylinder divided vertically into two equal segments 1A and 1B having inner and outer circumferential surfaces subjected to polarization treatment (poling) so that the polarization directions 20a and 20b are opposite, and coated with electrodes V. One end of the transmission shaft 2 is fitted into the hollow portion of the hollow cylindrical vibrator 1 while the outer circumferential surface of the vibrator 1 is held in a fixed state. Conversely, one end of the transmission shaft 2 may be fitted about the hollow cylindrical vibrator 1 while the inner circmferential surface of the vibrator 1 is held in a fixed state (not shown). In this state, the vibrator 1 is electrically driven at the inner or outer circumferential surface thereof with the center thereof being a vibrating axis. Therefore, the vibration of the vibrator 1 is transmitted to the detector member 3 through the transmission shaft 2 in the same manner as described above, thereby detecting the viscous resistance of the liquid 9 at the circumferential surface 3a of the detector member 3.

As has been described in the foregoing description, the viscosity detector according to the present invention uses an electromechanical vibrator vibrating about its central axis to vibrate a detector member about the same axis, thereby detecting the viscous resistance of liquid at the circumferential surface of the detector member. Therefore, the present invention can effectively avoid the generation of a wave in the liquid, which would be a disturbance factor that is known to be produced when using a commercially available vibrator vibrating in its direction of thickness and can measure the viscosity over a wider range with a high degree of precision. When the liquid samples having viscosities which are very close to each other are to be measured, the viscosities can be precisely obtained.

Furthermore, according to the present invention, since the circumferential surface of a detector member detects the viscous resistance, the detecting surface area can be sufficiently provided and can be adjusted with ease by selecting the diameter and length of the detector member. Therefore, the detector member can be suitably designed in accordance with the object of measurement.

In addition, according to the present invention, the vibration of the detector member can be obtained with ease, the detection structure is very simple, and a viscosity detector that is small and light as compared with a conventional one using a vibration motor can therefore be provided.

What is claimed is:

1. A viscosity detector for detecting the viscosity of a liquid, said detector comprising:
   an inertia mass fixed in the detector;
   an electromechanical vibrator rigidly connected to said inertia mass and having a central axis, said vibrator capable of vibrating about the central axis;
   a transmission shaft connected to said vibrator at one end thereof and extending coaxially from said vibrator;
   a detector member connected to said transmission shaft at the other end thereof and extending coaxially therefrom, said detector member vibratable via said transmission shaft by said vibrator above the central axis thereof, and said detector member having an outer circumferential surface along which viscous resistance offered by a liquid acts when the detector member is immersed in the liquid and vibrated thereby detecting the viscous resistance offered by the liquid;
   said vibrator including converting means for converting viscous resistance of a liquid acting on the detector member at said circumferential surface thereof into an electric signal corresponding to the viscosity of the liquid; and
   resonant frequency establishing means for establishing a desired resonant frequency of said vibrator, said resonant frequency establishing means comprising a mass having a predetermined moment of inertia and fitted around said transmission shaft at a location thereof spaced from said vibrator by a distance corresponding to said desired resonant frequency.

2. A viscosity detector as claimed in claim 1, wherein said converting means comprises piezoelectric members.

* * * * *